United States Patent [19]

Duysings et al.

[11] Patent Number: 4,850,001
[45] Date of Patent: Jul. 18, 1989

[54] ORIFICE BLOCKAGE DETECTION SYSTEM

[75] Inventors: Frederik M. H. J. Duysings; David B. Baxter, both of Houston, Tex.; Chandler H. Barkelew, Eugene, Oreg.

[73] Assignee: Shell Oil Company, Houston, Tex.

[21] Appl. No.: 75,361

[22] Filed: Jul. 20, 1987

[51] Int. Cl.⁴ .................. G01N 23/06; G01B 15/02
[52] U.S. Cl. .................................. 378/54; 378/56; 250/356.1; 250/363.01
[58] Field of Search .................. 110/101 CA, 165 R; 250/356.1, 357.1, 363 R, 363.1; 378/51, 52, 62, 54, 56

[56] References Cited

U.S. PATENT DOCUMENTS

| | | | |
|---|---|---|---|
| 2,118,651 | 5/1938 | Mucchi | 110/165 R |
| 2,896,084 | 7/1959 | MacDonald | 250/356.1 |
| 3,164,019 | 1/1965 | Burgwald et al. | 378/51 |
| 3,519,815 | 7/1970 | Sandbrook | 378/51 |
| 3,582,647 | 6/1971 | Figuet et al. | 378/51 |
| 3,796,692 | 3/1974 | Foltz et al. | 378/52 |
| 4,160,373 | 7/1979 | Fastaia et al. | 73/23 |
| 4,261,554 | 4/1981 | Eysh | 266/272 |
| 4,282,433 | 8/1981 | Löffel et al. | 250/356.1 |
| 4,395,958 | 8/1983 | Caffyn et al. | 110/165 R |
| 4,433,242 | 2/1984 | Harris et al. | 378/52 |
| 4,511,371 | 4/1985 | Blaskowski | 110/165 R |

*Primary Examiner*—Janice A. Howell
*Assistant Examiner*—John C. Freeman

[57] ABSTRACT

A method and apparatus for detecting blockage of an orifice, such as slag tap of a gasifier, by positioning at least one radiation source and detector in diametrically opposing positions outside the slag tap and out of contact with the molten slag.

8 Claims, 1 Drawing Sheet

U.S. Patent   Jul. 18, 1989   4,850,001

ORIFICE BLOCKAGE DETECTION SYSTEM

BACKGROUND OF THE INVENTION

This invention relates to a process for combusting carboncontaining fuel with an oxygen-containing gas in a reactor under high pressures and temperatures in which the gas formed is removed at the top of the reactor and slag at the bottom of the reactor. The invention also relates to a reacotr for use in the process.

Since carbon-containing fuel is usually of mineral origin, it invariably also contains, in addition to carbon and hydrogen, a certain quantity of inorganic, incombustible material often referred to by the term "ash" which is separated during the complete or partial combustion of mineral fuel. The residual ash collects as a molten slag and iron in the hearth of the reactor from which it is discharged (commonly known as slag-tapping) downward through a slag tap outlet or orifice in the hearth into a water bath.

Sometimes the molten slag and iron solidifies within the slag tap orifice thus causing a blockage of the orifice which prevents a satisfactory slag tapping operation.

Conventional systems for observing slag tap blockage, such as gas temperature and heat flux measurements below the slag tap do not permit observation within the slag tap. Additionally, optical systems are negatively influenced by high concentrations of coal and ash particles above and below the slag tap region.

The present invention is directed to overcoming this problem in the prior art.

Applicants are not aware of any prior art which, in their judgment as persons skilled in this particular art, would anticipate or render obvious the present invention. However, for the purpose of fully developing the background of the invention, and establishing the state of requisite art, the following art is set forth: U.S. Pat. Nos. 4,261,554; 4,160,373; 2,896,084 and 4,282,433.

SUMMARY OF THE INVENTION

The primary purpose of the present invention relates to detecting blockage of a slag tap region of a vessel, such as a gasifier, operated under elevated temperature and pressure.

Preferably, such an apparatus includes: at least one radiation source located outside of the orifice and out of contact with the stream to direct radiation to penetrate at least a portion of the stream being conveyed, at least one radiation detector located substantially diametrically opposite the radiation source and outside of the orifice to receive radiation from the source at least a portion of which is transmitted through the stream, means for transmitting the radiation from the source to the detector, means for receiving radiation by the detector, means for transmitting signals relative to radiation received by the detector to means for converting the signals to yield measurements of radiation intensity, means for converting signals from the detector to a signal relative to radiation intensity, means for comparing the radiation intensity indication with a preselected value, and means for determining a characteristic of the blockage.

Preferably, a method for detecting blockage includes: positioning at least one radiation source located outside of the orifice and out of contact with the stream to direct radiation to penetrate at least a portion of the stream being conveyed, positioning at least one radiation detector located substantially diametrically opposite the radiation source and outside of the orifice to receive radiation from the source at least a portion of which is transmitted through the stream, transmitting the radiation from the source to the detector, receiving radiation by the detector, transmitting signals relative to radiation received by the detector to a means for converting the signals to yield measurements of radiation intensity, converting signals from the detector to a signal relative to radiation intensity, comparing the radiation intensity indication with a preselected value, and determining a characteristic of the blockage.

The various features of novelty which characterize the invention are pointed out with particularity in the claims forming a part of this disclosure. For a better understanding of this invention, its operating advantages and specific objects obtained by its uses, reference may be made to the accompanying drawings and descriptive matter in which there are illustrated preferred embodiments of the invention.

DESCRIPTION OF A PREFERRED EMBODIMENT

Figure 1:
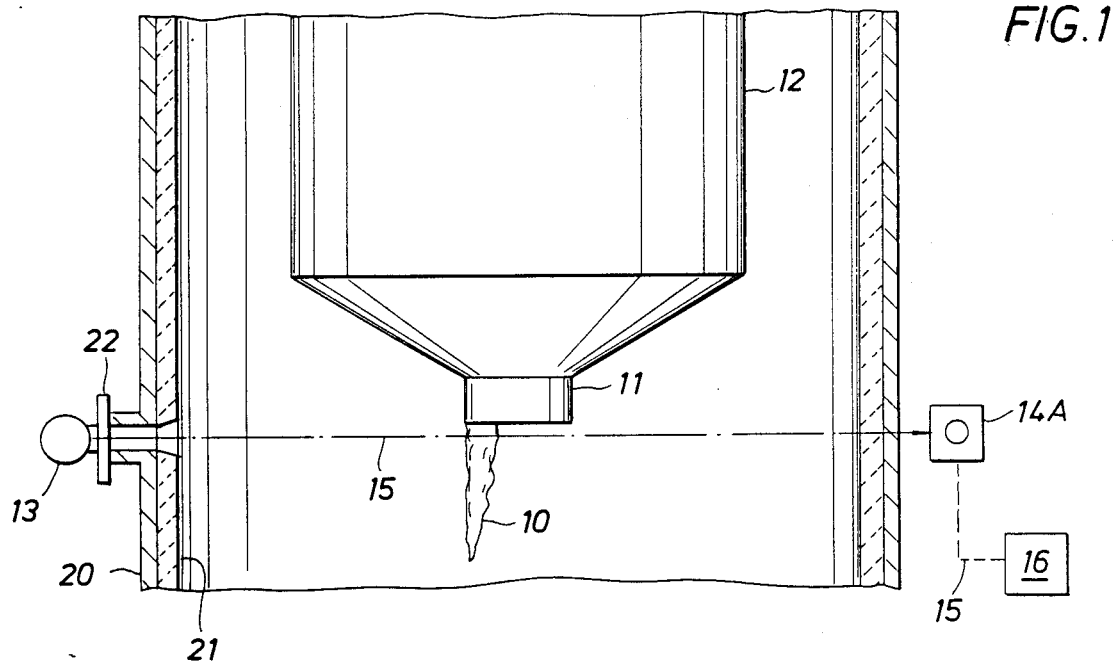
FIG. 1 illustrates a preferred embodiment of the present invention.

Generation of synthetic gas occurs by combining carbon-containing fuel, such as coal, at relatively high temperatures in the range of 800 to 1000° C. and at a pressure range of from about 1–200 bar in the presence of oxygen or oxygen-containing gases in a reactor known as a gasifier, hereinafter sometimes referred to as a gasifier.

Steam, carbon monoxide, carbon dioxide, and oxygen-containing gases including air, oxygen-enriched air, and oxygen are optionally diluted with nitrogen and/or other inert gases.

The combustion may be complete or partial, the object of the combustion process being in the first case the production of heat, for example, for direct or indirect power generation and in the second case, the production of synthesis gas mainly consisting of carbon monoxide and hydrogen.

In the present invention, the ash which is the inorganic, incombustible material is separated from the fuel during the combustion or gasification of the mineral fuel. Depending on the operating conditions under which combustion or gasification takes place, in particular the temperature and the quality of the fuel, the ash is mainly obtained in solid or liquid condition or in a combination thereof. The larger part of the liquid ash obtained, further referred to as slag, flows along the reactor wall, through a discharge opening, often referred to as a slag tap, and is generally collected in a water bath located below the slag tap of the reactor, where the slag is collected, solidified, and subsequently discharged.

The slag tap should be rather narrow for various reasons. First, the escape of unconverted coal through the discharge opening should be avoided as much as possible. Second, the slag discharge opening should prevent water vapor formed during the cooling of the slag in the water bath from entering the reactor in excessive quantities. The penetration of the water vapor into the reactor could unfavorably affect the combustion process when it enters the reactor in substantial quantities. Moreover, the water vapor will have a solidifying effect on the slag in the reactor resulting in the slag flow to the slag discharge opening being reduced.

Depending upon the conditions in the reactor such as the type of carbon-containing fuel used, the slag will more or less easily flow to the slag tap and subsequently enter the cooling water bath. However, if the slag flow through the slag tap is reduced it may cause blockage of the slag tap. If the slag tap becomes blocked, the slag will accumulate in the reaction zone and the combustion process must be interrupted in order to clean the slag tap. Apart from the loss of production involved in interrupting the process, there is also poor accessibility of the reactor owing to the high process temperature and pressure, which will result in the cleaning of the slag tap being a complicated and time consuming matter.

In the present invention, at least one gamma ray source positioned outside of the slag tap and out of contact with said slag, directs radiation to penetrate the slag that is being conveyed. At least one radiation detector, located substantially diametrically opposite said radiation source and outside of said tap, receives radiation from the source, at least a portion of which is transmitted through said slag.

Based on the radiation received, a comparison with a calibration standard having a known blockage allows for the determination of the blockage of the slag tap.

An advantage of the present invention is the possibility of controlling the blockage of the slag tap thus extending the time periods between shutdown of the gasifier and providing the flexibility of operating the process under various conditions such as a range of pressures, temperatures, and types of coal which characteristically produce different amounts of slag.

A further advantage of the present invention is the capability of utilizing one radiation source and one detector, therefore greatly simplifying the invention. Since the primary purpose of the invention is to detect the initiation of slag tap blockage, an indication of the density of the slag tap blockage at various locations with the slag tap is not essential and hence a dual source system for creating a stereoscopic view is not required.

Although the invention is described hereinafter primarily with reference to particulate coal, the method and apparatus according to the invention are also suitable for other catalysts or finely divided particulate reactive solids such as those which can be combusted, as for example, lignite, anthracity, bituminous, brown coal, soot, petroleum coke, and the like. Preferably, the size of the solid carbonaceous fuel is such that about 90 percent by weight of the fuel has a particle size smaller than No. 6 mesh (A.S.T.M.).

Having thus generally described the apparatus and method of the present invention, as well as its numerous advantages over the art, the following is a more detailed description thereof, given in accordance with specific reference to the drawings. However, the drawings are of the process flow type in which auxiliary equipment, such as pumps, compressors, cleaning devices, etc. are not shown. All values are merely exemplary or calculated.

Figure 2:
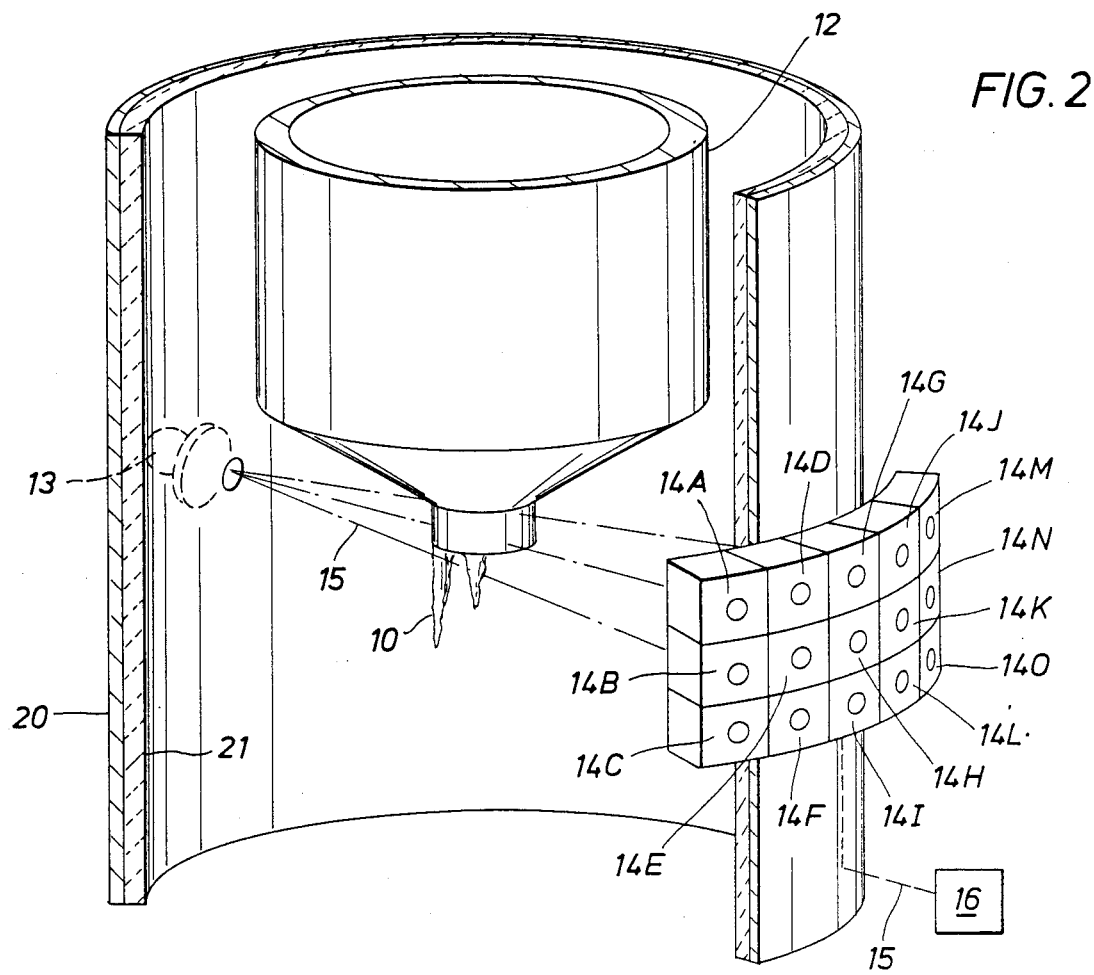
FIG. 2 illustrates the present invention with an array of detectors.

Referring to FIG. 1 of the drawing, an apparatus for detecting at least partial blockage of flow of a fluidic stream, such as molten slag 10, within an orifice, such as a slag tap 11, of a vessel operated at elevated temperature, pressure, and coal suspension density, such as a gasifier 12, preferably includes one radiation source, preferably a gamma ray source 13, and a detector 14A both located outside of the tap 11 and out of contact with the slag 10. This requirement is necessitated, in part, due to the elevated operating temperatures and pressures as previously mentioned. In the present invention, a sufficiently large Cobalt 60 or Cesium 137 source could be used together with one, or preferably an array, of scintillation detectors which are shown in FIGS. 1 and 2 as 14A-140. Cobalt 60 is preferred to penetrate the pressurized walls 20 and refractory lining 21 which are each at least about 60 mm thick.

Additionally, it is preferable not to place any obstructions in the slag tap region to avoid obstruction of the tap 11 for the reasons previously stated.

Furthermore, gamma ray radiation, as opposed to optical methods making use of infrared, UV, or visible light radiation, is preferred due to the high attenuation created by the coal and ash particles within the gasifier 12. In particular, the concentration of the coal and ash particles can be as high as 0.2 kg of coal and ash for each kg of synthesis gas.

Electromagnetic radiation in the short wavelength region, such as from a gamma ray source, behaves more as though it is composed of particles instead of waves. Because of this effect, the attenuation of this radiation is dependent on the density and atomic number of the attenuator, and not (as with longer wavelength radiation) on the physical shape of the attenuator. Therefore, gamma radiation can principally be used to detect slag tap conditions in the gasifier, without interference by ash, slag, and steam particles in the syngas.

In the present invention, the source 13 is positioned to direct radiation, shown for ease of illustration as a partially dashed line 15, to penetrate at least a portion of the slag tap 11. It may be mounted to the pressurized walls 20 of the gasifier 12 via a flange and nozzle arrangement 22 or placed in close proximity to the walls 20.

A detector 14A is located to receive radiation from the source 13 at least a portion of which is transmitted through the slag 10, the refractory material 21, and the walls 20. When slag tap 11 blockage occurs, the detector 14 will receive less radiation because of the additional attenuation of the slag. The additional detectors 14B-140, shown in FIG. 2, can be used to assist in determining characteristics of the blockage across the slag tap such as the position, rate of increase or decrease, and thickness of the blockage.

Signals 15 relative to the radiation received by the detector 14A are transmitted from the detector 14A to a means for converting the signals to yield measurements of radiation intensity, such as a signal processor/transmitter 16 generating an output signal being a function of the radiation intensity as measured by the detector. For example, a processor/transmitter such as Texas Nuclear Model SGD manufactured by Texas Nuclear Co. could be used in the present invention or this function could be performed in any other manner well known to the art.

The processor/transmitter 16 converts signals from the detector 14A to a signal relative to the radiation attenuation. This signal can then be displayed in either a digital or analog mode so as to compare the measured radiation attenuation indication with a preselected value to determine the characteristic blockage as previously mentioned.

It is preferred that the source and detector of the present invention are calibrated on a tap having a known blockage, say prior to using the present invention on a tap having flowing slag.

The accuracy of the present invention can be further improved by employing a means for reducing the scatter in the radiation received by the detector 14 from sources other than radiation not in direct line with the source by using means such as a collimator or any other means well known to the art.

Upon determining the characteristics of the blockage, the present invention can be used to control, and possibly prevent, the blockage of the slag 10 in the slag tap 11. For example, a signal (not shown) can be transmitted from the controller 16 to change the ratio of oxygen to coal introduced to the gasifier. As previously mentioned, the atmosphere of the gasifier should preferably be a reducing environment. Means for selectively controlling the weight ratio of oxygen to the coal and gas mixture introduced to the gasifier 12 is desirable. Preferably, the ratio is maintained so that the ratio of oxygen to moisture and ash free coal is in the range of 0.6 to 1.2, more preferably 0.8 to 0.9.

Additionally, the blockage of the slag tap can be controlled by adjusting the temperature of the gasifier. For example, adding calcium, say as limestone, reduces the melting temperature of the slag thereby reducing the viscosity of the molten slag during operation of the process.

Although the system for the present invention is shown in FIG. 1 in its distributed form as discrete components, it would be readily understood by those skilled in the art that these components could be combined into a single unit or otherwise implemented as may be most convenient for the particular application at hand. Furthermore, although the preferred embodiment has been shown as using an electronic transmitting system, it is also understood by those skilled in the art that the present invention could be effected using manual or pneumatic controls.

The foregoing description of the invention is merely intended to be explanatory thereof, and various changes in the details of the described method and apparatus may be made within the scope of the appended claims without departing from the spirit of the invention.

What is claimed is:

1. A method of detecting at least partial blockage of flow of molten slag within a slag tap of a gasifier operated at elevated temperature and pressure said method comprising the steps of:

positioning at least one radiation source located outside of said tap and out of contact with said slag to direct radiation so as to penetrate the cross-sectional area of said slag being conveyed;

positioning at least one radiation detector located substantially diametrically opposite said radiation source and outside of said tap to receive radiation from said source at least a portion of said radiation being transmitted through said slag;

transmitting said radiation from said source to said detector;

receiving radiation by said detector;

transmitting signals relative to radiation received by said detector to a means for converting said signals to yield measurements of radiation intensity;

converting signals from said detector to a signal relative to radiation intensity;

comparing said radiation intensity indication with a preselected value; and determining a characteristic of the blockage.

2. The method of claim 1 including calibrating said radiation source on a tap having a known blockage.

3. The method of claim 1 wherein said radiation detector comprises a plurality of detectors.

4. The method of claim 3 wherein said characteristic of blockage includes the thickness of said slag.

5. An apparatus for detecting at least partial blockage of flow of molten slag within a slag tap of a gasifier operated at elevated temperature and pressure said apparatus comprising:

at least one radiation source located outside of said tap and out of contact with said slag to direct radiation so as to penetrate the cross-sectional area of said slag being conveyed;

at least one radiation detector located substantially diametrically opposite said radiation source and outside of said tap to receive radiation from said source at least a portion of said radiation being transmitted through said slag;

means for transmitting said radiation from said source to said detector;

means for receiving radiation by said detector;

means for transmitting signals relative to radiation received by said detector to means for converting said signals to yield measurements of radiation intensity;

means for converting signals from said detector to a signal relative to radiation intensity;

means for comparing said radiation intensity indication with a preselected value; and means for determining a characteristic of the blockage.

6. The apparatus of claim 5 including means for calibrating said radiation source on a tap having a known blockage.

7. The apparatus of claim 5 wherein said detector is a plurality of detectors.

8. The apparatus of claim 7 wherein said characteristic of blockage is the thickness of said slag.

* * * * *